United States Patent [19]
Dall'Asta

[11] 3,959,266
[45] May 25, 1976

[54] PROCESS FOR THE CONVERSION OF PENICILLIN S-OXIDE INTO A CORRESPONDING DESATOXYCEPHALOSPORIN

[75] Inventor: Leone Dall'Asta, Milan, Italy

[73] Assignee: Societe Anonyme dite: CLIN-MIDY, Paris, France

[22] Filed: June 22, 1973

[21] Appl. No.: 372,638

[30] Foreign Application Priority Data
June 30, 1972 United Kingdom............... 30674/72

[52] U.S. Cl............................ 260/243 C; 260/239 A
[51] Int. Cl.²........................................ C07D 501/10
[58] Field of Search ................................. 260/243 C

[56] References Cited
UNITED STATES PATENTS
3,725,397  4/1973  Graham et al. ................. 260/243 C
3,725,399  4/1973  Ellerton et al. ................. 260/243 C

*Primary Examiner*—Nicholas S. Rizzo
*Assistant Examiner*—Mark L. Berch
*Attorney, Agent, or Firm*—Marn & Jangarathis

[57] ABSTRACT

A penicillin S-oxide is rearranged into the corresponding desacetoxycephalosporin compound by heating said penicillin S-oxide at a temperature of from 70 to 140°C in the presence of a sulfoxide of formula $R^1$-SO-$R^2$, preferably dimethyl sulfoxide, or a sulfonium or sulfoxonium salt of said sulfoxyde or a mixture of said sulfoxide and said sulfonium or sulfoxonium salt. The sulfoxide may act as reaction medium as well as reactant or an inert organic solvent may be used as a reaction medium.

12 Claims, No Drawings

PROCESS FOR THE CONVERSION OF PENICILLIN S-OXIDE INTO A CORRESPONDING DESATOXYCEPHALOSPORIN

FIELD OF THE INVENTION

The present invention is concerned with a process for the conversion of penicillin-type compounds into desacetoxycephalosporin-type compounds.

BACKGROUND OF THE INVENTION

U.S. Pat. No. 3,275,626 describes a process for converting a penicillin S-oxide into a desacetoxycephalosporin by heating said penicillin S-oxide at a temperature between 100° and 175°C under acid conditions. Modifications in the above-mentioned process are described in British patents 1,204,394 and 1,204,972 and in Belgian patents 745,845, 747,382 and 753,765.

Still according to the literature, good yields of cephalosporin compounds can be obtained by employing, as acid catalysts, hydrocarbon sulfonic acids or phosphoric acids (Belgian patent 747,118) optionally in the presence of a nitrogenous base (Belgian patent 747,119), or a O-mono substituted or O,O-diaryl substituted phosphoric acid, or its salts with nitrogenous bases (Belgian patent 747,120).

According to Belgian patent 763,104, the penicillin S-oxides can be arranged into the corresponding desacetoxycephalosporins by heating in the presence of a large excess of an organic, nitrogenous base and of an excess of a silicon compound having a silicon-halogen bond.

Thus, the methods of the prior art envisage the use of acid catalysts or the presence, at the same time, of an organic base and of a halogenated silicon derivative. According to these methods, the reaction takes place under rather strong conditions. Particularly, the S-oxides of the penicillins are subjected to prolonged heating at high temperatures in an acidic medium or, anyway, in the presence of large amounts of very reactive products. Under these conditions, both degradation of the penicillin nucleus and formation of undesired by-products occur. Actually, in order to reduce the formation of said by-products, it is suggested, according to the literature, that the reaction time should not be prolonged (U.S. Pat. No. 3,275,626), that thigh temperatures should be avoided (Belgian patent 763,104) and that the following conditions should concurrently be satisfied: careful choice of the reaction solvent, careful choice of the acid catalyst and careful choice of both the temperature and the reaction time (Belgian patent No. 747,118). Nevertheless, by operating according to the known methods a certain degradation of the penam nucleus cannot be avoided.

SUMMARY OF THE INVENTION

Surprisingly, it has now been found that the enlargement of the 2,2-dimethyl-penam ring occurs in a neutral medium excluding any acid catalyst if a penicillin S-oxide is heated in the presence of a sulfoxide, preferably dimethyl sulfoxide. Particularly, it has been discovered that the rearrangement of the penam nucleus can take place under neutral conditions by using a reagent, the dimethyl sulfoxide, which can also act as a reaction medium. Thus, the end reaction product can be easily isolated and purified.

Further, it has been found that the above reaction takes place in a very satisfactory manner in the presence of catalytic amounts of a sulfonium or sulfoxonium salt derived from said sulfoxide, which advantageously strengthen the electropositive character of the sulfur linked to the oxygen.

Finally, it has been found that good yields of 3-methyl-3-cephem compounds are obtained if the sulfoxide providing the rearrangement is used in the form of one of its above mentioned sulfonium or sulfoxonium derivatives.

Even though they are neutral agents, i.e. agents which do not give any acid reaction, the sulfoxides allow the rearrangement of the penicillin S-oxides into the corresponding desacetoxycephalosporins thanks to the positive character of their sulfur atom. The reaction mechanism is illustrated in the following scheme:

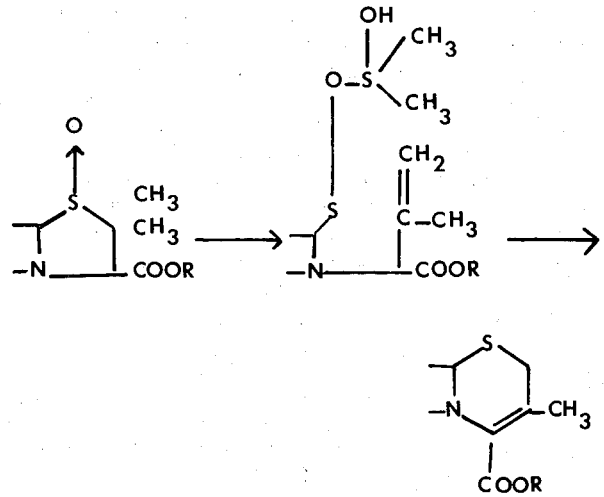

where the penam and cephem nuclei are only partially shown and dimethyl sulfoxide is given as a representative sulfoxide.

The present invention thus provides a process for the preparation of desacetoxycephalosporins which comprises heating a corresponding penicillin S-oxide at a temperature of from 70° to 140°C in the presence of (a) a sulfoxide of formula:

$$R^1-\overset{O}{\underset{\uparrow}{S}}-R^2 \qquad I$$

wherein $R^1$ is a mono- di- or trichloromethyl group, a lower alkyl group or a phenyl group, $R^2$ is a lower alkyl group or $R^1$ and $R^2$ together, represent a tetramethylene or pentamethylene group, (b) 0.01 to 0.3 molar equivalents, referred to the starting penicillin S-oxide, of a sulfonium or sulfoxonium salt obtained by reaction of said sulfoxide I with a compound selected from the group consisting of:

$b_1$ a hydrogen halide such as HCl, HBr or a salt thereof with tertiary organic bases such as pyridine, picolines, lutidines, quinoline, 1,2,3,4-tetrahydroquinoline, triethylamine and the like;

$b_2$ and oxygenated mineral or organic strong acid having a pKa lower than 1, such as nitric, sulfuric, p-toluenesulfonic, methanesulfonic acid and the like;

$b_3$ a (lower)alkyloxonium fluoborate, such as triethyloxonium fluoborate;

$b_4$ a sultone, such as propansultone, butan sultone and the sultone of α-hydroxy-o-toluenesulfonic acid, represented by the following general formula:

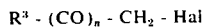

wherein Q is ethylene, n-propylene or o-phenylene;
b₅ a halogenated compound of the following general formula:

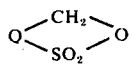

wherein Hal is a halogen atom such as chlorine, bromine and iodine, n is zero or 1 and $R^3$ is hydrogen, alkyl of from 1 to 5 carbon atoms or a phenyl group unsubstituted or substituted with 1 or 2 halogen atoms such as fluorine, bromine or chlorine or with 1 or 2 methoxy or nitro groups, $R^3$ being hydrogen only when n is zero; more particularly a lower alkyl halide (n = 0; $R^3 = H$, alkyl 1–5C) such as ethyl bromide, ethyl chloride, methyl iodide; a benzyl halide (n =0, $R^3$ = phenyl unsubstituted or substituted as above), such as benzyl chloride, benzyl bromide, p-nitrobenzyl bromide; or an α-haloketone (n = 1) such as α-chloroacetone, phenacyl bromide, p-nitrophenacyl bromide and the like, and (c) a mixture of said sulfoxide and said sulfonium or sulfoxonium salt.

DETAILED DESCRIPTION

The term "lower alkyl," as used herein, includes the saturated aliphatic hydrocarbon radicals containing from 1 to 6 carbon atoms, such as methyl, ethyl, propyl, isopropyl, n-butyl, sec-butyl, tert-butyl, isobutyl, n-pentyl, 2-methyl-butyl, n-hexyl, 2-methyl-pentyl, 3-methyl-pentyl and the like.

The sulfoxides of formula I giving a good rearrangement of the 2,2-dimethyl-penam nucleus, include, in a non-limitative way, dimethyl sulfoxide, diethyl sulfoxide, di-n-propyl sulfoxide, diisopropyl sulfoxide, chloromethyl-methyl sulfoxide and tetrahydrothiophene sulfoxide, dimethyl sulfoxide being particularly preferred.

The sulfonium or sulfoxonium salts derived from the sulfoxide I are prepared by reaction of said sulfoxides with the compounds b₁ to (b₅) above.

Thus, if the sulfoxide of formula I giving the rearrangement is treated with a compound of the group (b₁) or of the group (b₂) above, there is obtained a sulfonium salt of formula:

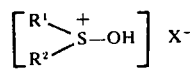

wherein X⁻ represents an anion of a halogenated acid or of an oxygenated mineral or organic strong acid having a pKa lower than 1 and $R^1$ and $R^2$ are as defined above. Among the products of this type, the dimethylsulfonium chloride and bromide, which are obtained as very hygroscopic solids by treating dimethyl sulfoxide with gaseous HCl or HBr at a temperature of about 0°C up to saturation, are preferred.

By reacting a sulfoxide of formula I with a tri(lower) alkyloxonium fluoborate (compounds of group b₃), there is obtained a sulfonium fluoborate of formula:

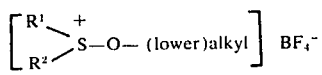

wherein $R^1$ and $R^2$ are defined as above. Among the products of this type, the dimethylsulfonio-oxyethyl-fluoborate is particularly preferred.

The product obtained by reacting a sulfoxide of formula I with a sultone of the formula II above, such as propansultone, butansultone or the sultone of α-hydroxy-o-toluenesulfonic acid (compounds of group b₄), is an inner sulfonium salt characterised by the following formula:

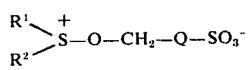

wherein $R^1$, $R^2$ and Q are as defined above. Among the products of this type, the dimethylsulfonio 3-oxypropyl sulfonate is particularly suitable. However, it is possible to prepare the corresponding sulfoxonium salt, characterized by the formula:

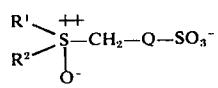

by protracting the reaction time or by operating in the heating.

By treating a sulfoxide of formula I with a halogenated compound of the group (b₅) included in formula III above, but other than an alkyl iodide, there is obtained a sulfonium halide characterised by the following formula:

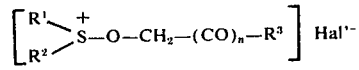

wherein $R^1$, $R^2$, $R^3$ and n are as defined above and Hal·⁻ is a chloro, bromo or iodo ion, Hal·⁻ being other than iodo ion when $R^3$ is hydrogen or alkyl 1-5C and n is zero. When the halogenated compound of the group b₅) is a lower alkyl iodide (formula III, $R^3$ = H, alkyl 1-5C, n = 0, Hal· = I), there is obtained a sulfoxonium salt of formula:

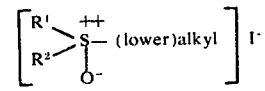

which catalyses the reaction in a satisfactory manner. Among the products obtained from the sulfoxides I and the compounds of group (b₅), the sulfonium salts derived from dimethyl sulfoxide and phenacyl, p-nitrophenacyl and p-nitrobenzyl bromide are particularly preferred.

Said sulfonium and sulfoxonium salts are represented, in a general way, by the following formulae:

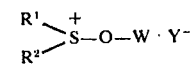 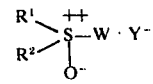

sulfonium salt    sulfoxonium salt

X    XI wherein $R^1$ and $R^2$ have the above-stated meaning; W is hydrogen, a $R^3$-(CO)$_n$-CH$_2$-group, in which $R^3$ and n are defined and limited as above, or a group-CH$_2$-Q-SO$_3^-$; and $Y^-$ represents a halogen anion or an anion of a mineral or organic strong acid having a pKa lower than 1 or the anion $BF_4^-$, $Y^-$ being absent when W is -CH$_2$-Q-SO$_3^-$.

The characteristics, the properties and the methods of preparation of the sulfonium and sulfoxonium salts which are obtained by reacting a sulfoxide, more particularly the dimethyl sulfoxide, with the compounds of the types ($b_1$)-($b_5$) above are described in detail in the monograph "Dimethyl Sulfoxide" by Stanley W. Jacob, Edward E. Rosenbaum and Don C. Wood, vol. I, pages 63–69.

If as an agent for the rearrangement of the 2,2-dimethyl penam nucleus a sulfoxide as such is used, it may be employed in an equimolecular amount, referred to the starting penicillin S-oxide, although the proportions of each reactant are not critical and the reaction occurs regardless of the proportions of the reactants. It is preferred, however, in order to obtain maximum yields, to operate in the presence of a one mole excess of sulfoxide. In particular, proportions of 20–80 ml of sulfoxide per gram of penicillin S-oxide to be transposed, preferably 50 ml per gram, give the best results. In the particular case of the dimethyl sulfoxide, large molar excesses thereof may be used and the dimethyl sulfoxide itself may act as both reaction medium and reactant. When small quantities of sulfoxide are used, the reaction may be carried out in an inert solvent, preferably in a polar solvent, such as a ketone, preferably methyl isobutyl-ketone or cyclohexanone, dioxane, dimethyl formamide, dimethyl acetamide, hexamethylene phosphoro amide and the like.

The reaction temperature can vary from 70° to 140°C, preferably from 75° to 120°C. The heating can be prolonged up to 12 hours although, in general, no starting product can be detected in the reaction medium after a 1–6 hours heating at 75 to 120°C. Anyway, the reaction can be followed by examining samples of the medium on thin layer chromatography by utilising the solvents commonly used to this purpose.

If, as an agent for the rearrangement, there is used a sulfonium or sulfoxonium salt obtained by reaction of the chosen sulfoxide with the compounds of the types $b_1$ -($b_5$) above, said sulfonium or sulfoxonium salt is employed in an amount of the order of from 0.01 to 0.3 mole per mole of penicillin S-oxide to be rearranged, the best results being obtained when from 0.05 to 0.1 molar equivalents of sulfonium or sulfoxonium salt referred to the starting material are used. Since said sulfonium and sulfoxonium salts are generally solids, it is suitable to operate in a polar solvent as described above; particularly, a very interesting degree of rearrangement and a reasonable reaction rate are achieved by using a solvent which can attain 120°C at normal pressure such as methyl isobutyl ketone or dimethylacetamide.

If a mixture of a sulfoxide I and of its sulfonium or sulfoxonium salt is used as the agent for the rearrangement, the reaction may be carried out in a solvent as described above or the sulfoxide itself may also act as a solvent. In such a case, its sulfonium or sulfoxonium salt can be formed in situ by adding the corresponding product of the type ($b_1$)-($b_5$) to the sulfoxide I chosen as the reaction medium, preferably before the introduction of the starting penicillin S-oxide. This procedure is particularly useful when a derivative of the sulfoxide I with a halogenated compound of the type ($b_5$), such as phenacyl, p-nitrophenacyl or p-nitrobenzyl bromide, a (lower)alkyl oxonium fluoborate of the type ($b_3$) or a salt of a hydrogen halide with a tertiary organic base (product of the type $b_1$), such as pyridine hydrochloride, 2,6-lutidine hydrochloride and like is used.

The sulfonium or sulfoxonium salt to be used can also be prepared separately and then added to the reaction medium. This procedure is suitable when derivatives of the sulfoxides I with compounds of the types ($b_1$), ($b_2$) and ($b_4$) above are used.

As water forms during the reaction, it may be useful to provide for its elimination according to well known methods, for example by azeotropic distillation or by adding a dehydrating agent to the reaction medium or by introducing on the way of the refluxing vapors, a thimble filled for example with molecular sieves.

At the end of the reaction, the final product is in general easily isolable. To this purpose, the reaction mixture is poured into water or on cracked ice, the solid which separates is filtered off, washed and dried according to well known procedures. The pure products can be obtained from the raw materials by trituration in or recrystallization from suitable solvents such as, for example, acetonitrile, isopropanol, ethanol, 1,2-dimethoxyethane and the like. The end product can also be isolated by evaporating the solvent, preferably in vacuo and crystallizing as above.

The process of the present invention can be used for the rearrangement of the penicillins of the prior art, in the form of free acid or esterified, although it is preferred to use for the rearrangement esters of 6-acylamido-2,2-dimethyl penam-3-carboxylic acid S-oxides where the 6-acylamido radical can be one of the radicals of antibiotically active penicillins or of penicillins used as intermediates. Suitable acylamido radicals are the phenylacetamido, phenoxyacetamido, 2-phenoxypropionamido, 2-phenoxybutyramido, 2-phenoxyphenylacetamido, 5-methyl-3-phenyl-4-isoxazole carboxamido, 5-methyl-3-(o-chlorophenyl)-4-isoxazole carboxamido, 5-methyl-3-(2,6-dichlorophenyl)-4-isoxazole carboxamido, 2-ethoxy-1-naphthamido, 2,6-dimethoxybenzamido, N-methyl-2-(o-aminobenzamido)-phenylacetamido, N-methyl-2-(2-amino-5-nitrobenzamido)-phenylacetamido, N-benzylformamido, N-ethyl-2-phenylacetamido, N-isobutyl-2-phenoxyacetamido, phthalimido, α-(benzyloxycarbamoyl)-phenylacetamido, 2-thienylacetamido, 2-furylacetamido, 4-chlorophenylacetamido, 3-nitrophenylacetamido, 4-nitrophenylacetamido, 3-trifluoromethylphenyl-acetamido and 3-chlorophenylthioacetamido radicals. The acylamido radicals also include those in which the acylamido portion is a part of an etherocyclic nucleus, such as, for example, the 2,2-dimethyl-5-oxo-4-phenyl-1-imidazolidinyl, 2,2-dimethyl- 3-nitroso-5-oxo-4-phenyl-1-imidazolidinyl and 2,2-dimethyl-5-oxo-4-(p-hydroxyphenyl)-1-imidazolidinyl radicals. Preferred acylamido radicals for the rearrangement according to the present invention are the phenylacetamido, phenoxyacetamido, α-aminophenylacetamido and 2,2-dimethyl-3-nitroso-5-oxo-4-phenyl-1-imidazolidinyl and phthalimido radicals.

When the acylamido radical is α-aminophenylacetamido, the amino group should be protected by an easily removable group such as, for example, the benzyloxycarbonyl or trichloroethoxycarbonyl radical.

The ester in the 3-position of the starting penicillin S-oxide can be of very different nature. Particularly, the esters derived from lower alcohols, such as the methyl or ethyl ester are suitable. However, it is preferred to use esters which can be easily converted, by reduction or hydrolysis, into the corresponding free acid. Exemples of ester groups which can be easily hydrolysed or reduced include the 2,2,2-trichloroethyl, 2,2-dichloroethyl, p-methoxybenzyl, p-nitrobenzyl, p-nitrophenacyl, 3,5-dimethoxybenzhydryl, 2,4-dimethoxybenzhydryl, benzhydryl, phthalimidomethyl, succinimidomethyl, tert-butyl, tert-pentyl, tert-hexyl, 1,1-dimethyl-2-propenyl, 1,1-dimethyl-2-pentenyl, 1,1-dimethyl-2-propynyl, 1,1-dimethyl-2-butylnyl and 1,1-dimethyl-2-pentenyl.

The penicillin S-oxides used as starting materials in the process according to the present invention can be obtained from the corresponding penicillins by oxydation of the sulfur atom at the 1 position according to methods well known in the art. Suitable oxydizing agents are, for example, hydrogen peroxide, ozone, metaperiodic acid, peracetic acid, monoperphthalic acid, m-chloroperbenzoic acid and tert-butyl hypochlorite.

The following Examples illustrate the invention.

EXAMPLE 1

A mixture of 2.42 g (0.005 mole) of p-nitrobenzyl ester of penicillin G S-oxide in 125 ml of pure dimethyl sulfoxide is heated under stirring on an oil bath at 105°C for three hours. The reaction mixture is left to return to room temperature, then it is poured, slowly, with stirring, into 250 g of cracked ice. The solid which forms is filtered, washed with water and dried under 0.1 mmHg at room temperature, then it is crystallised from 1,2-dimethoxyethane. There is obtained 430 mg (18%) of p-nitrobenzyl 7β-phenylacetamido-3-methyl-3-cephem-4-carboxylate as a well crystallized product melting at 225°–227°C.

Thin layer chromatography (silica gel, reference Merck 60F 254, eluent: ethyl acetate - benzene 2:1):
only one spot : Rf 0.34
starting product : Rf 0.12
IR spectrum (chloroform) $\nu$ = 1775, 1725, 1675 and 1600 cm$^{-1}$

EXAMPLE 2

A mixture of 2.5 g (0.005 mole) of p-nitrobenzyl ester of penicillin V S-oxide in 125 ml of pure dimethyl sulfoxide is heated at 105°C for 4 hours. Following the same procedure of Example 1, there is obtained 600 mg (24.7%) of p-nitrobenzyl 7β-phenoxyacetamido-3-methyl-3-cephem-4-carboxylate melting at 190°–192°C after crystallisation from acetonitrile.

Thin layer chromatography (silica gel, reference Merck 60F 254, eluent: ethyl acetate - benzene 1:2):
only one spot : Rf 0.34
starting product : Rf 0.13
IR spectrum (chloroform) $\nu$ = 1780, 1725, 1690 and 1590 cm$^{-1}$
Determination of the real conversion rate: 34.5%.

EXAMPLE 3

A mixture of 2 g (0.004 mole) of p-nitrobenzyl ester of penicillin V S-oxide in 20 ml of pure dimethyl sulfoxide is heated at 100°C for 6 hours. The reaction mixture is then concentrated under reduced pressure, the residue is taken up with water, and the crude product is separated by filtration and dried under vacuum. After crystallisation from acetonitrile, 0.76 g (39% of theoretical) of p-nitrobenzyl 7β-phenoxyacetamido-3-methyl-3-cephem-4-carboxylate melting at 188°–190°C is obtained, identical to the product of Example 2.

EXAMPLE 4

A 700 mg (0.0014 mole) portion of p-nitrobenzyl ester of penicillin V S-oxide is added to 35 ml of tetrahydro-thiophene sulfoxide heated at 100°C. The reaction mixture is stirred at the same temperature for 4 hours, then it is left to return to room temperature and poured with stirring into 70 g of cracked ice. The solid which forms is filtered, washed with water and dried at room temperature under 0.5 mmHg in the presence of phosphoric anhydride. The p-nitrobenzyl 7β-phenoxyacetamido-3-methyl-3-cephem-4-carboxylate is obtained with a 28% conversion rate.

EXAMPLE 5

A 250 mg (0.0005 mole) portion of p-nitrobenzyl ester of penicillin V S-oxide is added to 12.5 ml of di-n-propyl sulfoxide heated at 100°C. After heating at the same temperature under stirring for 4 hours, the reaction mixture is left to return to room temperature. The dipropyl sulfoxide is evaporated under reduced pressure (0.5 mmHg) at 80°C to an oily residue yielding a 15% conversion rate into p-nitrobenzyl 7β-phenoxyacetamido-3-methyl-3-cephem-4-carboxylate.

EXAMPLE 6

A mixture of 2.42 g (0.005 mole) of p-nitrobenzyl ester of penicillin G S-oxide in 125 ml of pure dimethyl sulfoxide containing 108 mg (0.0005 mole) of p-nitrobenzyl bromide is heated under stirring on an oil bath at 105°C for 3 hours. The mixture is left to return to room temperature and then is poured with stirring into 250 g of ice. The solid is filtered, dried at room temperature under 0.1 mmHg, and crystallized from 1,2-dimethoxyethane. There is so obtained 730 mg (32%) of chromatographically pure p-nitrobenzyl 7β-phenylacetamido-3-methyl-3-cephem-4-carboxylate, identical to the product of Example 1.

Only one spot on thin layer chromatography.

EXAMPLE 7

A mixture of 2.5 g (0.005 mole) of p-nitrobenzyl ester of penicillin V S-oxide in 125 ml of pure dimethyl sulfoxide containing 108 mg (0.0005 mole) of p-nitrobenzyl bromide, is heated under stirring on an oil bath at 105°C for 4 hours. The mixture is left to return to room temperature and then is poured, while stirring, into 250 g of ice. The solid is filtered, dried at room temperature under 0.1 mmHg and crystallized from acetonitrile. There is so obtained 1.04 g (43%) of chromatographically pure p-nitrobenzyl 7β-phenoxyacetamido-3-methyl-3-cephem-4-carboxylate, identical to the product of Example 2.

Real conversion rate: 51%.

By operating under the same conditions, but utilising different amounts of p-nitrobenzyl bromide ($pNO_2C_6H_4CH_2Br$) there is obtained the p-nitrobenzyl 7β-phenoxyacetamido-3-methyl-3-cephem-4-carboxylate in the yields given in Table I hereinbelow.

TABLE I

| Example | Amount of $pNO_2C_6H_4CH_2Br$ (mg) | Yield of pure isolated product | Real conversion rate |
|---|---|---|---|
| 8 | 216 | 31% | 41% |
| 9 | 54 | 49% | 62% |

EXAMPLE 10

A mixture of 1 g of p-nitrobenzyl ester of penicillin V S-oxide in 50 ml of pure diisopropyl sulfoxide containing 43 mg of p-nitrobenzyl bromide is heated at 105°C for 4 hours. By operating as in Example 7 there is obtained the p-nitrobenzyl 7β-phenoxyacetamido-3-methyl-3-cephem-4-carboxylate with a conversion rate of 19%.

EXAMPLE 11

To a solution of 432 mg of p-nitrobenzyl bromide in 500 ml of pure dimethyl sulfoxide heated at 100°C there is added 10 g (0.02 mole) of p-nitrobenzyl ester of penicillin G S-oxide. The reaction mixture is heated at 100°C for 3 hours under stirring, then it is left to return to room temperature and poured slowly into 1000 g of cracked ice and stirred. A solid forms, which is filtered, washed with water, dried on $P_2O_5$ at 0.5 mmHg and room temperature. By crystallizing the crude product isolated from the dimethoxyethane, 3.5 g (37%) of p-nitrobenzyl 7β-phenylacetamido-3-methyl-3-cephem-4-carboxylate are obtained as a product showing only one spot on thin layer chromatography and having the physical characteristics described in Example 1.

Real conversion rate determined on the crude reaction product: 53%.

EXAMPLE 12

A mixture of 125 ml of pure dimethyl sulfoxide containing 108 mg (0.0005 mole) of p-nitrobenzyl bromide is heated on an oily bath at 100°C, then there is added 2.4 g (0.005 mole) of trichloroethyl ester of penicillin G S-oxide. The heating is continued for 5 hours at the same temperature. After cooling to 20°C, the solution is poured into 250 g of cracked ice, which is stirred until complete fusion. The solid obtained is filtered, thoroughly washed with water and dried on $P_2O_5$ at reduced pressure and room temperature. After purification by washing with ethyl ether and recrystallization from isopropanol, 0.69 g (30% yield) of 2,2,2-trichloroethyl 7β-phenylacetamido-3-methyl-3-cephem-4-carboxylate is obtained, m.p. 161°–162°C.

Thin layer chromatography (silica F 254; eluent: benzene - ethyl acetate 2:1): Rf = 0.74;

IR spectrum (KBr) $\nu$ = 3320, 1765, 1725, 1675, 1625 and 1530 $cm^{-1}$

Conversion rate determined on the crude reaction product: 56%.

By operating under the same conditions, but varying the amount of p-nitrobenzyl bromide ($pNO_2C_6H_4CH_2Br$) and the time of heating, there is obtained the 2,2,2-trichloroethyl 7β-phenylacetamido-3-methyl-3-cephem-4-carboxylate in the yields given in Table II hereinbelow.

TABLE II

| Ex. | Amount of $pNO_2C_6H_4CH_2Br$ (mg) | Time of heating | Yield of pure isolated product | Real conversion rate |
|---|---|---|---|---|
| 13 | 54 | 5 h | 20% | — |
| 14 | 108 | 5 h | 43% | 56% |
| 15 | 108 | 6 h 30 | 33% | 41% |
| 16 | 216 | 5 h | 20% | — |

EXAMPLE 17

A 2.48 g (0.005 mole) portion of p-nitrobenzyl 6-phthalimido penicillinate S-oxide is added to a mixture of 0.1 g of p-nitrobenzyl bromide in 125 ml of pure dimethyl sulfoxide heated at 100°C. The reaction mixture is stirred at 100°C for 4 hours, then it is left to return to 20°C, poured into 250 g of cracked ice and stirred. The solid which precipitates is filtered, washed with water and dried on $P_2O_5$ at 20°C under 0.5 mm Hg, then it is crystallized from acetonitrile. 0.85 g (35%) of p-nitrobenzyl 7β-phthalimido-3-methyl-3-cephem-4-carboxylate melting at 186°–187°C are so obtained, showing only one spot on thin layer chromatography (silica Merck F 254; eluent : benzene - ethyl acetate 2:1); Rf = 0.55 (starting product 0.22).

IR spectrum (chloroform) $\nu$ = 1785, 1775 and 1720 $cm^{-1}$

Real conversion rate determined on the crude product: 55%.

EXAMPLE 18

To a solution of 122 mg of p-nitrophenacyl bromide in 125 ml of pure dimethyl sulfoxide heated to 100°C, there is added 2.5 g (0.005 mole) of p-nitrobenzyl ester of penicillin V S-oxide. The reaction mixture is stirred at 100°C for 4 hours, then it is left to return to room temperature, poured slowly into 250 g of cracked ice and stirred. The solid which forms is filtered, washed with water, dried on $P_2O_5$ under 0.5 mmHg and room temperature. By crystallization from acetonitrile, there is obtained 800 mg of p-nitrobenzyl 7β-phenoxyacetamido desacetoxycephalosporanate melting at 190°–192°C (yield : 33%) and having the physical and spectral characteristics identical to those given in Example 2.

Real conversion rate determined on the crude reaction product: 48%.

EXAMPLE 19

A 2.5 g (0.0052 mole) portion of p-nitrobenzyl ester of penicillin G S-oxide is added to a solution of 61 mg of p-nitrophenacyl bromide in 125 ml of pure dimethyl sulfoxide heated to 100°C. The reaction mixture is stirred for 3 hours at this temperature, then it is left to return to room temperature, poured slowly into 250 g of cracked ice and stirred. The solid which forms is filtered, washed with water, dried on $P_2O_5$ at 0.5 mmHg and room temperature and crystallized from dimethoxymethane. There is so obtained 900 mg of p-nitrobenzyl 7β-phenylacetamido-3-methyl-3-cephem-4-carboxylate (p-nitrobenzyl 7β-phenylacetamido-desacetoxycephalosporanate), melting at 225°–227°C (yield: 38%) and having the same physical and spectral characteristics of the product described in Example 1.

Real conversion rate determined on the crude reaction product: 53%.

By operating under the same conditions, but varying the amount of p-nitrophenacyl bromide, the p-nitrobenzyl 7β-phenylacetamido-3-methyl-3-cephem-4-carboxylate is obtained in the yields given in Table III hereinbelow.

TABLE III

| Example | Amount of p-nitrophenacyl bromide (g) | Yield of crystallized product | Real conversion rate |
|---|---|---|---|
| 20 | 0.061 | 38% | 53% |
| 21 | 0.122 | 29% | 46% |

EXAMPLE 22

A 2.42 g (0.005 mole) portion of penicillin G S-oxide p-nitrobenzyl ester is added to 0.11 g of trimethyl sulfoxonium iodide, obtained by reacting dimethyl sulfoxide with methyl iodide, and to 125 ml of dimethyl sulfoxide heated to 100°C. The reaction mixture is stirred at 100°C for 3 hours, left to return to 20°C, poured into 250 g of cracked ice and stirred. The solid which precipitates is filtered, washed with water and dried on $P_2O_5$ at 0.5 mmHg and 20°C, and crystallized from dimethoxyethane. There is so obtained 0.70 g of p-nitrobenzyl 7β-phenylacetamido-3-methyl-3-cephem-4-carboxylate melting at 225°–227°C. Only one spot on T.L.C.

By operating as described hereinabove, but utilising 0.011 g of trimethyl sulfoxonium iodide there is obtained 0.93 g of the same product.

EXAMPLE 23

A mixture of 2.5 g (0.005 mole) of p-nitrobenzyl ester of penicillin V S-oxide in 125 ml of pure dimethyl sulfoxide containing 79 mg (0.005 mole) of dimethyl sulfonium bromide (prepared by treating the dimethyl sulfoxide with HBr gas at 0°C until saturation and utilized as such) is heated on an oil bath at 105°C for 3 hours. After being returned to room temperature, the reaction mixture is poured into 250 g of cracked ice with stirring. The solid which forms is filtered, dried at 0.1 mmHg and room temperature and then crystallized from acetonitrile.

There is so obtained 900 mg (37%) of pure p-nitrobenzyl 7β-phenoxyacetamido-3-methyl-3-cephem-4-carboxylate, identical to the product of Example 2.

Real conversion rate starting from the crude reaction product: 46%. phenoxyactamido-3-methyl-By operating under the same conditions, but varying the amount of the dimethyl sulfonium bromide and the time of heating, the pure p-nitrobenzyl 7β-phenoxyacetamido-3-methyl-3-cephem-4-carboxylate is obtained in the yields given in Table IV hereinbelow.

TABLE IV

| Ex. | Amount of dimethyl sulfonium bromide (mg) | Time of heating | Yield of pure isolated product | Real conversion rate |
|---|---|---|---|---|
| 24 | 79 | 5 h | 28% | 41% |
| 25 | 158 | 2 h | 32% | — |

EXAMPLE 26

A 2.5 g (0.005 mole) portion of p-nitrobenzyl ester of penicillin V S-oxide in 125 ml of pure dimethyl sulfoxide containing 0.1 g of dimethyl sulfonio 3-oxypropylsulfonate (Bull.Soc.Chim.Belges 74, 450; 1965) is heated under stirring on an oil bath at 105°C for 4 hours. The reaction mixture is left to return to room temperature and poured with stirring into 250 g of cracked ice. The solid so obtained is filtered, dried in a high vacuum without heating and crystallized from acetonitrile to give a 38% yield of p-nitrobenzyl 7β-phenoxyacetamido-3-methyl-3-cephem-4-carboxylate identical to the product described in Example 2.

Real conversion rate determined on the crude reaction product: 47%.

By operating under the same conditions but varying the amount of the dimethyl sulfonio-3-oxypropylsulfonate the time of heating and the temperature, there is obtained the pure nitrobenzyl 7β-phenoxyacetamido-3-methyl-3-cephem-4-carboxylate in the yields given in Table V hereinbelow.

TABLE V

| Example | Amount of dimethyl sulfonio 3-oxy-propylsulfonate (g) | Time of heating | T°C | Yield of pure isolated product | Real conversion rate |
|---|---|---|---|---|---|
| 27 | 0.2 | 4 h | 105 | 40% | 48% |
| 28 | 0.2 | 3 h | 105 | 38% | 49% |
| 29 | 0.1 | 2 h | 120 | 28% | 37% |
| 30 | 0.2 | 2 h | 120 | 26% | 36% |

EXAMPLE 31

By operating as described in Example 17, but by substituting 0.2 g of dimethyl sulfonio 3-oxy-propylsulfonate for p-nitrobenzyl bromide, there is obtained, after crystallization from acetonitrile, 41% of p-nitrobenzyl 7β-phthalimido-3-methyl-3-cephem-4-carboxylate. Real conversion rate on the crude reaction product: 53%.

EXAMPLE 32

A 2.4 g portion of 2,2,2-trichloroethylester of penicillin G S-oxide is added, at 100°C, to 125 ml of dimethyl sulfoxide containing 0.1 g of dimethyl sulfonio 3-oxy-propylsulfonate. The reaction mixture is stirred at 100°C for 5 hours. After cooling, the solution is poured with stirring into 250 g of cracked ice. The solid which forms is filtered, washed with water and dried under vacuum in the presence of $P_2O_5$. The dry product is crystallized from isopropanol giving 0.8 g (31%) of pure trichloroethyl 7β-phenylacetamido-3-methyl-3-cephem-4-carboxylate, identical to the product described in Example 12.

EXAMPLE 33

To a solution of 190 mg of triethyloxonium fluoborate in 125 ml of purified dimethyl sulfoxide heated to 100°C, there is added 2.5 g (0.005 mole) of p-nitrobenzyl ester of penicillin V S-oxide. The reaction mixture is stirred 3 hours at that temperature, then it is left to return to room temperature and poured slowly into 250 g of cracked ice and stirred. The solid which forms is filtered, washed with water, dried on $P_2O_5$ at 0.5 mmHg and room temperature. After crystallization from acetonitrile, there is obtained a 33% yield of pure p-nitrobenzyl 7β-phenoxyacetamido-3-methyl-3-cephem-4-carboxylate, identical to the product of Example 2. Real conversion rate determined on the crude reaction product: 46%.

EXAMPLE 34

A mixture of 2.5 g (0.005 mole) of p-nitrobenzyl ester of penicillin V S-oxide in 60 ml of pure isobutyl methyl ketone containing 100 mg of dimethylsulfonio 3-oxypropyl sulfonate are heated under stirring at reflux for 6 hours. The reaction mixture is left to return to room temperature, washed twice with 40 ml of water. The organic phase is dried on magnesium sulfate and evaporated under vacuum to dryness. The gummy residue so obtained is crystallized from acetonitrile, giving a 27% yield of pure p-nitrobenzyl 7β-phenoxyacetamido-3-methyl-3-cephem-4-carboxylate.

By operating under the same conditions, but varying the nature and the amount of the sulfonium salt, the p-nitrobenzyl 7β-phenoxyacetamido-3-methyl-3-cephem-4-carboxylate is obtained in the yields given in Table VI hereinbelow.

TABLE VI

| Ex. | Sulfonium salt nature | amount (mg) | Yield of pure isolated product | Real conversion rate |
|---|---|---|---|---|
| 35 | dimethylsulfonio 3-oxy propylsulfonate | 100 | 27% | — |
| 36 | dimethylsulfonio 3-oxy propylsulfonate | 1000 | 29% | 41% |
| 37 | dimethylsulfonium bromide | 160 | 18% | — |

EXAMPLE 38

To a boiling (120°C) solution of 100 mg of dimethyl sulfonium bromide in 125 ml of isobutyl methyl ketone there is added 2.5 g (0.0052 mole) of p-nitrobenzyl ester of penicillin G S-oxide. The reaction mixture is stirred 15 hours at 120°C, then it is left to return to room temperature, washed with water and dried. The solvent is evaporated to dryness under vacuum and the residue is crystallized from dimethoxyethane. There is so obtained 288 mg (12%) of p-nitrobenzyl 7β-phenylacetamido-3-methyl-3-cephem-4-carboxylate; m.p. 225°–227°C. Only one spot on T.L.C.

EXAMPLE 39

To a solution of 560 mg of chloromethyl-methyl sulfoxide in 125 ml of isobutyl methyl ketone heated at reflux (120°C) there is added 2.42 g (0.005 mole) of p-nitrobenzyl ester of penicillin G S-oxide. The reaction mixture is stirred 8 hours at 120°C, then it is left to return to room temperature, washed with water and dried. The solvent is evaporated to dryness under reduced pressure and the residue is crystallized from dimethoxyethane. There is so obtained the p-nitrobenzyl 7β-phenylacetamido-3-methyl-3-cephem-4-carboxylate; m.p. 225°–227°C in 19% yield. The product is identical to that described in Example 1. Only one spot on T.L.C.

EXAMPLE 40

To a mixture of 1.0 g of dimethylsulfonio 3-oxypropylsulfonate in 70 ml of isobutyl methyl ketone heated to 120°C, there is added 2.42 g (0.005 mole) of p-nitrobenzyl 6-phthalimido penicillanate S-oxide. The reaction mixture is stirred at 120°C for 6 hours, then it is left to return to 20°C, washed with water in a separating funnel and dried on magnesium sulfate. After crystallization from acetonitrile there there is obtained 1.01 g (42%) of p-nitrobenzyl 7β-phthalimido-3-methyl-3-cephem-4-carboxylate identical to the product of Example 17; m.p. 184°–187°C. Only one spot on T.L.C.

EXAMPLE 41

To 120 ml of dioxane containing 0.2 g of dimethyl sulfonio 3-oxypropylsulfonate and 1 ml of pure dimethyl sulfoxide there is added 2.4 g of 2,2,2-trichloroethyl ester of penicillin G S-oxide. The reaction mixture is heated 4 hours at reflux. The solvent is evaporated under vacuum and the residue washed with water, dried under vacuum in the presence of $P_2O_5$ and easily crystallized from isopropanol. There is so obtained a 23% yield of pure trichloroethyl 7β-phenylacetamido-3-methyl-3-cephem-4-carboxylate in 23% yield; m.p. 160°C. Only one spot on T.L.C.

EXAMPLE 42

To 180 ml of isobutyl methyl ketone containing 0.2 g of dimethyl sulfonio 3-oxypropylsulfonate and 1 ml of pure dimethyl sulfoxide there is added 2.4 g of 2,2,2-trichloroethyl ester of penicillin G S-oxide. The reaction mixture is heated 5 hours at 120°C, washed with water and dried on magnesium sulfate. After evaporation of the solvent and crystallization of the residue from isopropanol, there is obtained a 21% yield of trichloroethyl 7β-phenylacetamido-3-methyl-3-cephem-4-carboxylate, identical to the product of Example 12. Only one spot on T.L.C.

EXAMPLE 43

A 2.5 g (0.005 mole) portion of p-nitrobenzyl ester of penicillin V S-oxide is added to 60 ml of pure isobutyl methyl ketone containing 80 mg of dimethyl sulfonium bromide and 1 ml of pure dimethyl sulfoxide. By refluxing the reaction mixture 6 hours and then operating as described in Example 34, there is obtained a 35% yield of pure p-nitrobenzyl 7β-phenoxyacetamido-3-methyl-3-cephem-4-carboxylate, identical to the product of Example 2.

In the same manner, by substituting 0.1 g of dimethyl sulfonio 3-oxy-propyl sulfonate for dimethyl sulfonium bromide, after 4 hours of refluxing, the pure product is isolated in 41% yield.

EXAMPLE 44

Into a 250 ml flask fitted with a Dean-Stark water trap and a vertical condenser there is introduced 80 ml of benzene, 60 ml of dimethylacetamide and 0.4 g of dimethyl sulfonio 3-oxypropyl sulfonate. The mixture is heated at reflux for 3 hours in order to attain complete anhydration, then 10 g of p-nitrobenzyl ester of penicillin V S-oxide is added. The resulting mixture is refluxed 6 hours and 0.4 ml of water are collected in the trap. The solvent is evaporated under vacuum (60°C/0.5 mmHg) to a solid residue weighing 10.72 g, which is taken up with 50 ml of a benzene — ether 1:1 mixture, and stirred for one hour. The solid so obtained is filtered, washed with ether and dried. Thus, there is obtained 8.1 g (85%) of a white product, melting at 190°–192°C identical to the p-nitrobenzyl 7$\beta$-phenoxyacetamido-3-methyl-3-cephem-4-carboxylate of Exemple 2. Only one spot on T.L.C.

By operating as described above, but replacing the dimethylacetamide with the same amount of ciclohexanone and heating for 36 hours at reflux, the same product is isolated in 71% yield.

EXAMPLE 45

Into a 750 ml flask fitted with a Dean-Stark water trap and a vertical condenser there is introduced 200 ml of isobutyl methyl ketone, 200 ml of anhydrous benzene and 0.4 g of dimethyl sulfonio 3-oxypropyl sulfonate. After 3 hours heating, 10 g of p-nitrobenzyl ester of penicillin V S-oxide are poured into the mixture. By operating as in Example 44, there is obtained 3.88 g (40.5%) of pure p-nitrobenzyl 7$\beta$-phenoxyacetamido-3-methyl-3-cephem-4-carboxylate; m.p. 190°–192°C. Only one spot on T.L.C.

EXAMPLE 46

By operating as described in Example 44, by heating 2.48 g of p-nitrobenzyl 6-phthalimido penicillanate S-oxide, in a mixture of 20 ml of benzene, 15 ml of dimethyl acetamide and 100 mg of dimethylsulfonio 3-oxypropyl sulfonate, there is obtained 1.2 g (52%) of pure p-nitrobenzyl 7$\beta$-phenylacetamido-3-methyl-3-cephem-4-carboxylate; m.p. 186°–187°C identical to the product of Example 17. Only one spot on T.L.C.

EXAMPLE 47

Into a 250 ml flask fitted with a Dean-Stark water trap and a vertical condenser there is introduced 80 ml of benzene, 60 ml of dimethylacetamide, 1 ml of dimethyl sulfoxide and 0.4 g dimethylsulfonio 3-oxy propylsulfonate. After 3 hours at reflux, 10 g of p-nitrobenzyl ester of penicillin V S-oxide are added to the mixture. The heating is continued for 6 hours at reflux and 0.4 ml of water are collected in the trap. The solvent is evaporated under vacuum (60°C/0.5 mmHg) to a solid residue which is taken up with 50 ml of a mixture benzene — ether 1:1 and stirred for one hour. The solid so obtained is filtered, washed with ether and dried. Thus, there is obtained 7.75 g (81.5%) of pure p-nitrobenzyl 7$\beta$-phenoxyacetamido-3-methyl-3-cephem-4-carboxylate; m.p. 190°–192°C. Only one spot on T.L.C.

EXAMPLE 48

To a mixture of 15 ml of anhydrous dimethylacetamide and 20 ml of anhydrous benzene, there is added 0.1 g of dimethylsulfonio 3-oxy propylsulfonate. After a 1 hour heating, with azeotropic entrainement by means of a Dean-Stark water trap, there is added 2.62 g of p-nitrophenacyl ester of penicillin G S-oxide (m.p. 178°–180°C, prepared by action of p-nitrophenacyl bromide on the triethylamine salt of penicillin G S-oxide in acetone). The reaction mixture is subjected to azeotropic distillation for 6 hours, then the solvent is evaporated under vacuum and the residue is tritured in a mixture benzene — ether 1:1. By crystallization from acetonitrile of the raw solid product thus obtained, 961 mg (38%) of pure p-nitrophenacyl 7$\beta$-phenylacetamido-3-methyl-3-cephem-4-carboxylate are obtained; m.p. 192°–195°C. Only one spot on T.L.C.

EXAMPLE 49

A mixture of 2.62 g of p-nitrophenacyl ester of penicillin G S-oxide in 60 ml of pure isobutyl methyl ketone containing 0.1 g of dimethylsulfonio 3-oxy-propylsulfonate is heated at reflux, under stirring, for 6 hours. The reaction mixture is left to return to room temperature, then twice washed with 40 ml of water. The organic phase is dried on magnesium sulfate and evaporated under vacuum to dryness. The residue so obtained is crystallized from acetonitrile to give 640 mg (25%) of p-nitrophenacyl 7$\beta$-phenoxyacetamido-3-methyl-3-cephem-4-carboxylate, identical to the product of Example 48. Only one spot on T.L.C.

EXAMPLE 50

To a mixture of 50 ml of dimethyl sulfoxide and 0.05 g of pyridine hydrochloride, there is added, at 100°C, 2.4 g of trichloroethyl ester of penicillin G S-oxide and the heating is continued at the same temperature. The reaction is followed by thin layer chromatography using a mixture benzene - ethyl acetate 2:1 as eluting solvent and the reagent iodine/azide (Russel, Nature 1960, 186, 788) to visualize the spots. After 6 hours heating, no traces of the starting material are present in the reaction mixture which is then poured into icewater. The milky suspension so obtained is treated with diluted hydrochloric acid in order to facilitate the separation of a solid product which by crystallization from hot absolute ethanol gives 730 mg (32%) of pure trichlorethyl 7$\beta$-phenylacetamido-3-methyl-3-cephem-4-carboxylate, identical to the product of Example 12.

By operating under the same conditions, but substituting 132 mg of 2,6-lutidine hydrochloride, 165 mg of quinoline hydrochloride and, respectively, 169 mg of 1,2,3,4-tetrahydroquinoline hydrochloride for pyridine hydrochloride, there is obtained 600 mg (25%) 560 mg (24%) and, respectively, 780 mg (33%) of pure product.

EXAMPLE 51

A 2.5 g (0.005 mole) portion of p-nitrobenzyl ester of penicillin V S-oxide is added to 125 ml of pure dimethyl sulfoxide containing 0.1 g of dimethyl sulfoxonio propylsulfonate (Bull, Soc. Chim. Belges 74, 450; 1965). The resulting mixture is heated under stirring on an oil bath at 105°C for 4 hours, then it is left to return to room temperature. By operating as described in Example 26, 900 mg (37%) of p-nitrobenzyl 7$\beta$-phenoxyacetamido-3-methyl-3-cephem-4-carboxylate, identical to the product of Example 2, are obtained. Only one spot on T.L.C.

EXAMPLE 52

A mixture of 15 ml of dimethylacetamide, 20 ml of anhydrous benzene, 0.1 g of dimethylsulfonio 3-oxy propylsulfonate is heated at reflux for one hour in an apparatus fitted with a Dean-Stark trap in order to eliminate the last traces of water. Then there is added 1.83 g of penicillin V S-oxide and the resulting mixture is heated 6 hours at reflux with azeotropic elimination of the water of the reaction. The solvent is evaporated under vacuum, the residue is extracted with ethyl acetate and the solution obtained is filtered. The organic phase is extracted with an aqueous normal solution of sodium bicarbonate. The aqueous phase is treated with hydrochloric acid 10% up to pH 3, extracted with ethyl acetate and dried on magnesium sulfate. After evaporation of the solvent under vacuum, the residue is treated with 5 ml of methanol containing 0.003 mole of dibenzylamine and the solution so obtained is left to stand 48 hours at −15°C. There are so obtained 325 mg (12%) of the dibenzylamine salt of the 3-methyl-3-cephem-7β-phenylacetamido-4-carboxylic acid, as a crystalline solid melting at 134°–136°C.

I claim:

1. A process for converting a penicillin S-oxide selected from the group consisting of a 6-acylamidopenicillanic acid S-oxide and esters thereof, into the corresponding desacetoxycephalosporin, comprising:
effecting said conversion by heating said penicillin S-oxide to a temperature of 70° to 140°C in the presence of an amount of dimethyl sulfoxide effective for converting said penicillin S-oxide to the corresponding desacetoxycephalosporin.

2. The process of claim 1 wherein said conversion is effected also in the presence of from 0.01 to 0.3 molar equivalent, referred to the starting penicillin S-oxide of at least one sulfonium salt having a structural formula selected from the group consisting of

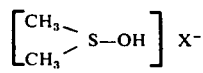         (i)

wherein X⁻ is selected from the group consisting of anions of hydrochloric, hydrobromic, nitric, sulfuric, p-toluene sulfonic and methane-sulfonic acid.

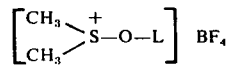         (ii)

wherein L is an alkyl group having from 1 to 6 carbon atoms.

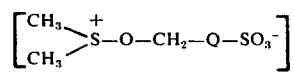         (iii)

wherein Q is selected from the group consisting of ethylene, n-propylene and O-phenylene; and

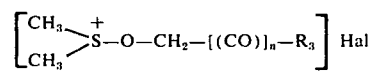         (iv)

wherein Hal is selected from the group consisting of chloro-, bromo- and iodo-
n is 0 or 1

$R_3$ is selected from the group consisting of hydrogen, alkyl having from 1 to 5 carbon atoms, phenyl, mono- and di- nitro substituted phenyl, mono- and di- halo substituted phenyl wherein halo is selected from the group consisting of chloro-, bromo- and iodo and mono- and di- methoxy substituted phenyl, and when $R_3$ is hydrogen or an alkyl group and n is O, Hal is other than iodo, and $R_3$ is hydrogen only when n is O.

3. The process of claim 2 wherein the sulfonium salt has the formula:

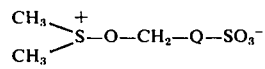

wherein Q is ethylene.

4. The process of claim 1 wherein the conversion is effected with only dimethyl sulfoxide.

5. The process of claim 2 wherein the sulfonium salt is

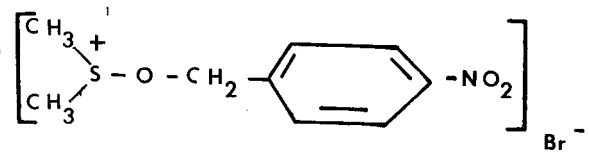

6. The process of claim 2 wherein the sulfonium salt is

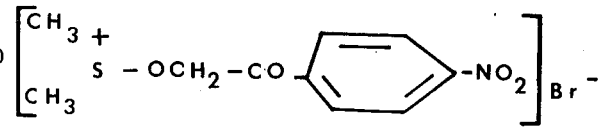

7. The process of claim 1 wherein the dimethyl sulfoxide is present in an amount of from 20 to 80 ml per gram of starting penicillin S-oxide.

8. The process of claim 2 wherein the conversion is effected in the presence of a mixture of dimethyl sulfoxide and dimethyl sulfonium bromide.

9. The process of claim 2 wherein the conversion is effected in the presence of a mixture of dimethyl sulfoxide and dimethyl sulfonio oxyethyl fluoborate.

10. The process of claim 1 wherein the penicillin S-oxide is an ester of penicillin V S-oxide.

11. The process of claim 1 wherein the penicillin S-oxide is an ester of penicillin G S-oxide.

12. The process of claim 1 wherein the penicillin S-oxide is 6-phthalimido penicillanic acid.

* * * * *

UNITED STATES PATENT OFFICE
CERTIFICATE OF CORRECTION

Patent No. 3,959,266  Dated May 25, 1976

Inventor(s) Leone Dall'Asta

It is certified that error appears in the above-identified patent and that said Letters Patent are hereby corrected as shown below:

In the title, "DESATOXYCEPHALOSPORIN" should be -- DESACETOXY-CEPHALOSPORIN --.

Column 1, line 28, "arranged" should be -- rearranged --;
  line 46, "thigh" should be -- high --.

Column 3, line 46, delete " $b_1$ to ($b_5$ )" and insert -- ($b_1$ to $b_5$ ) --.

Column 5, line 66, "in situ" should be -- *in situ* --

Column 7, line 12, "Exemples" should be -- Examples --.

Signed and Sealed this

Fourteenth Day of December 1976

[SEAL]

Attest:

RUTH C. MASON
*Attesting Officer*

C. MARSHALL DANN
*Commissioner of Patents and Trademarks*